United States Patent [19]

Eberwine

[11] Patent Number: 5,514,545
[45] Date of Patent: May 7, 1996

[54] METHOD FOR CHARACTERIZING SINGLE CELLS BASED ON RNA AMPLIFICATION FOR DIAGNOSTICS AND THERAPEUTICS

[75] Inventor: James Eberwine, Philadelphia, Pa.

[73] Assignee: Trustees of the University of Pennsylvania, Philadelphia, Pa.

[21] Appl. No.: 97,129

[22] Filed: Jul. 26, 1993

Related U.S. Application Data

[63] Continuation-in-part of Ser. No. 897,249, Jun. 11, 1992, abandoned.

[51] Int. Cl.$^6$ .............................. C12Q 1/68; C12P 19/34
[52] U.S. Cl. .................... 435/6; 435/15; 435/91.1; 435/91.21; 435/91.2; 435/91.5; 435/91.51
[58] Field of Search .................... 435/6, 91.2, 15, 435/91.1, 91.21, 91.5, 91.51; 935/78

[56] References Cited

U.S. PATENT DOCUMENTS 5,021,335  6/1991  Tecott et al. ........................ 435/6
5,168,038  12/1992  Tecott et al. ........................ 435/6

OTHER PUBLICATIONS

Eberwine et al., *PNAS* 89, 3010–3014, 1992.
Sambrook et al., "*Molecular Cloning*", Cold Spring Harbor Laboratory Press, 1989.
Eberwine et al., in "*Methods of Enzymology*", Wu ed., vol. 216, pp. 80–100, 1992.
Van Gelder et al., *PNAS* 87, 1663–1667, 1990.
Chang et al., *Biochem. Biophys. Res. Comm.* 157(2), 698–704, 1988.
Liu et al., *J. Virol. Methods* 35, 227–236, 1991.

*Primary Examiner*—W. Gary Jones
*Assistant Examiner*—Kenneth R. Horlick
*Attorney, Agent, or Firm*—Jane Massey Licata

[57] ABSTRACT

A method is provided for characterizing cells at the molecular level by amplifying RNA from selected single cells by microinjecting primer, nucleotides and enzyme into acutely dissociated cells to produce amplified antisense RNA; reamplifying the amplified antisense RNA (aRNA) produced by using random hexanucleotides to prime cDNA synthesis from aRNA, and then detecting messages in the amplified RNA. The invention is useful for characterization of cell identity or physiological state.

6 Claims, 7 Drawing Sheets

METHOD FOR CHARACTERIZING SINGLE CELLS BASED ON RNA AMPLIFICATION FOR DIAGNOSTICS AND THERAPEUTICS

CROSS REFERENCE TO RELATED APPLICATIONS

This application is a continuation-in-part of U.S. application Ser. No. 897,249, filed Jun. 11, 1992, abandoned, which is incorporated herein by reference.

FIELD OF THE INVENTION

The present invention relates to a method of characterizing cells by generating an expression profile which inventories RNA present in a specific cell under specific conditions.

BACKGROUND OF THE INVENTION

The central nervous system (CNS) is made up of a large number of interacting neuronal systems and these, in turn, are comprised of heterogeneous cell populations. Analysis of cellular diversity within a given system has been based largely on the presence of morphological and protein markers. However, individual cells may differ functionally based on their localization, synaptic and glial interactions and the cadre of genes which are expressed. These factors combine to determine the cellular and functional identity of individual cells within the CNS. This interaction is so complex that the variety of cellular identities is certainly far greater than has been recognized to date using established methods.

The ability to experimentally manipulate single cells using whole cell and patch clamp techniques has provided a specificity and sensitivity of analysis which has permitted the characterization of the electrophysiological properties of single cells. While tremendous strides have been made on the electrophysiological front, little progress has been made in understanding the regulation of mRNA levels in individual cells. The limitation has been that most biochemical and molecular biological studies have used complex neural systems as sources of RNA. These include brain slices or dissected tissue samples and heterogeneous populations of cells grown in culture. Such preparations suffer from the large amount of tissue that is required for analysis, thereby making analysis of cellular specificity problematic. While in situ hybridization can be used to assess gene expression in individual fixed cells, this approach is limited in its ability to depict accurately the entire mRNA population of the cell. Furthermore, it has not been possible to obtain electrophysiological recordings from the individual cell of interest prior to the in situ hybridization. Examining the entire mRNA population of a cell is an important aspect of cellular responsiveness since mRNA level changes often dictate changes in protein concentrations. If mRNA levels within the cell can be detected, then it may be possible to predict protein production and cellular responsiveness to various exogenous stimuli.

The amount of DNA within a single cell is estimated to be between 0.1 and 1 picograms and, as such, is difficult to manipulate experimentally. The most commonly employed amplification procedure is the polymerase chain reaction (PCR). To utilize this technology, one must first make cDNA from RNA isolated from a single cell using reverse transcriptase followed by the addition of a primer site to the 3'-end of the first strand cDNA, most commonly by the action of terminal transferase. The amplification process utilizes this added sequence and the poly-A tail of second strand cDNA as priming sites for the amplification process. PCR has been utilized to amplify cDNA populations encoding mRNA from as few as 1000 cells. Tam et al., *Nuc. Acids Res.*, 17:1269 (1989); Belyavski et al., *Nuc. Acids Res.*, 17:2919–2932 (1989).

PCR technology, however, suffers from several drawbacks which limit its utility for studies of single cells. PCR works best when small regions of a few hundred nucleotides are being amplified. When larger cDNAs are amplified, there is a disproportionate decrease in the level of amplification such that longer cDNAs are not amplified at the same rate as shorter cDNAs. In addition, the error rate of the enzyme most commonly used for PCR, namely Taq polymerase, is high enough such that errors are estimated to be incorporated once per 1,000 bases of incorporation. With such an error rate, it is certain that most PCR-amplified cDNAs will contain several erroneous bases. While these problems can be dealt with if anticipated, it is not possible to easily address the difference in the efficiency of the amplification of different cDNA molecules. Even a small difference in efficiency will result in several thousand fold differential representation of these cDNAs in the cDNA population after as few as 30 rounds of amplification. It is possible that with technological improvements in PCR amplifications, it could become a useful approach in the routine isolation of individual cDNAs from single cells of the nervous system. However, these technological problems currently limit the overall usefulness of PCR in the study of gene expression in single cells.

The technique of amplified, antisense RNA (aRNA) synthesis (VanGelder et al., *Proc. Natl. Acad. Sci. USA*, 87:1663–1667 (1990)) circumvents many of these problems by facilitating the linear amplification of large mRNAs with few errors. The first step is the synthesis of an oligo-d(T) primer that is extended at the 5'-end with a T7 RNA polymerase promoter. This oligonucleotide can be used to prime the poly-A+-mRNA population for cDNA synthesis. After the first strand cDNA is synthesized, the second-strand cDNA is made using either "Gubler-Hoffman" for RNA in solution (Gubler, V. and Hoffman, B. *Genet.*, 25:263–269 (1983), or "hairpinning" for tissue sections (Maniatis et al., *Cell*, 15:687–701 (1978)). This is followed by a brief S1-nuclease treatment and "blunt-ending" with T4-DNA polymerase. The cDNA is now ready for amplification using the T7 RNA polymerase promoter (Melton et al., *Nuc. Acids Res.*, 12:7035–7056 (1984); Nielsen, D. A. and Shapiro, D. J., *Nuc. Acids Res.*, 14:5936–5940 (1986)) to direct the synthesis of RNA. The RNA made using this technique is antisense to the poly-A+ RNA and can be used directly as a probe, or it can be cloned into plasmid or phage vectors using standard techniques (Sambrook et al., *Molecular Cloning*, 2nd Ed., Cold Spring Harbor Press, 1989).

U.S. Pat. No. 5,021,335 (Tecott et al.) discloses in situ transcription for cDNA synthesis in cells and tissues. Fixed tissue sections are contacted with a nucleotide primer under hybridizing conditions and then contacted with reverse transcriptase under primer-extension conditions. Labeling with radioactive nucleotides to follow primer extension in the tissue section may be performed using standard techniques. The transcript may then be isolated by elution and used in cloning, expression, etc.

Although aRNA provides a means for amplifying RNA populations, it is extremely difficult to isolate RNA from a single cell. The primary obstacle to the isolation of RNA from a single cell is the tendency of RNA to nonspecifically interact with plastic and glass.

SUMMARY OF THE INVENTION

A method for characterizing cells at the molecular level is provided. To assess the relative amounts of mRNAs for specific proteins and to demonstrate the expressed component of the genetic complement, a primer and an enzyme such as reverse transcriptase is injected via patch pipette into a single, live acutely dissociated brain cell to produce cDNA from the existing mRNA. The cDNA from selected cells is transcribed into RNA and subsequently amplified so that messages in the amplified RNA can be detected.

DETAILED DESCRIPTION OF THE INVENTION

The present invention provides a novel method for accurately assessing the relative amounts of mRNAs for specific proteins and to demonstrate the expressed component of the genetic complement or "expression profile" of individual brain cells. The method comprises injecting, via patch pipette, a primer which is an amplification oligonucleotide and an enzyme such as reverse transcriptase into single live acutely dissociated brain cells such as hippocampal cells. Useful amplification oligonucleotides include oligo-dT-T7, oligo-dT-T3 and oligo-dT-$SP_6$ oligonucleotides.

Figure 1B:
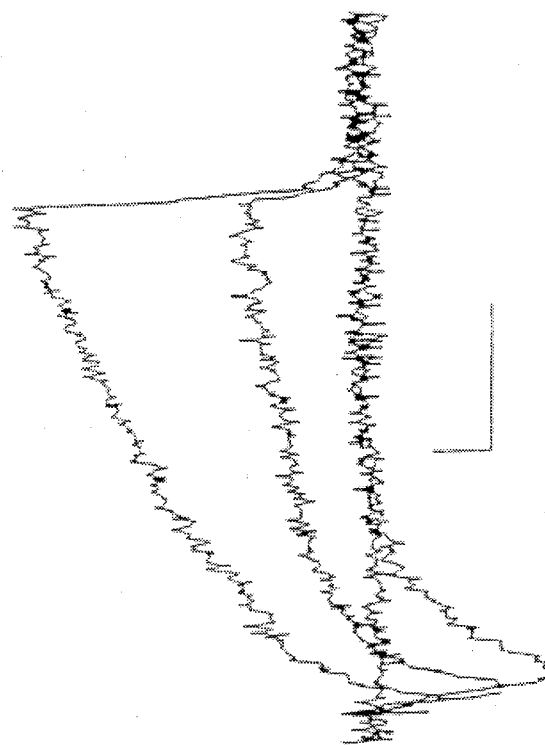
As shown in FIG. 1B, the efficiency of the patch clamp procedure was assessed by monitoring macroscopic inward and outward currents in response to depolarizing command potentials under voltage clamp.
Figures 1, 1A:
FIG. 1A is representative of cells used.

In our experiments, solitary hippocampal neurons were obtained following acute dissociation of the postnatal rat hippocampus using a procedure originally designed for obtaining solitary retinal cells (Yeh et al., *Visual Neurosci.*, 4:349–357 (1990). Cells which exhibited morphological features characteristic of pyramidal cells, i.e., a large (15–30 micrometer somal diameter), pyramidal or oval shaped soma with apical and basal dendrites which are truncated to varying degrees, were used. The cell illustrated in FIG. 1A is representative.

Patch-clamp recording pipets were filled with solution containing the amplification oligonucleotide and reverse transcriptase and, in the whole-cell patch-clamp recording mode, the pipet contents readily dialyzed into these cells. As a routine step, the efficiency of the patch clamp procedure was assessed by monitoring macroscopic inward and outward currents in response to depolarizing command potentials under voltage clamp (FIG. 1B).

In separate experiments, lucifer yellow was included in the pipet solution. It was determined that intracellular dialysis was complete by 3–5 minutes following rupture of the membrane to achieve the whole-cell mode. By the end of 5 minutes, the cytoplasmic contents were drawn into the recording pipet by applying negative pressure (suction). Occasionally, it was necessary to create a larger opening by carefully breaking the tip of the recording pipet to facilitate withdrawal of the cytoplasmic contents. One of the distinct advantages of this procedure over standard isolation procedures is that the components that direct cDNA synthesis are brought into immediate contact with the mRNA in a self-contained environment, namely the cell and the patch pipette, which likely increases the efficiency of conversion of mRNA into cDNA.

A single round of aRNA amplification yielded approximately 2000 fold amplification of the original mRNA concentration. This calculation is based upon the amount of synthesized aRNA relative to that presumed to be present within a cell (0.1 picogram). The amplified aRNA at this point did not contain enough material to make a useful cDNA library and, furthermore, it was difficult to use as a probe. To generate more aRNA, the initial aRNA population was reamplified. This was accomplished by using random hexanucleotides to prime cDNA synthesis from the aRNA by reverse transcriptase. Second strand cDNA synthesis takes advantage of the fact that the cDNA has a poly-dA tail. The oligo-dt-T7 amplification primer can be hybridized to the cDNA and will serve as a primer for second strand cDNA synthesis. While second strand cDNA is synthesized from the oligo-dT primer, the initial first strand cDNA is extended at the 3'-end by copying of the antisense strand of the T7 promoter region of the amplification primer. In this manner, the T7 promoter is added to the aRNA population (see FIG. 2). This second round aRNA amplification routinely results in $>1 \times 10^6$ fold amplifications of the original starting material.

Figure 3:
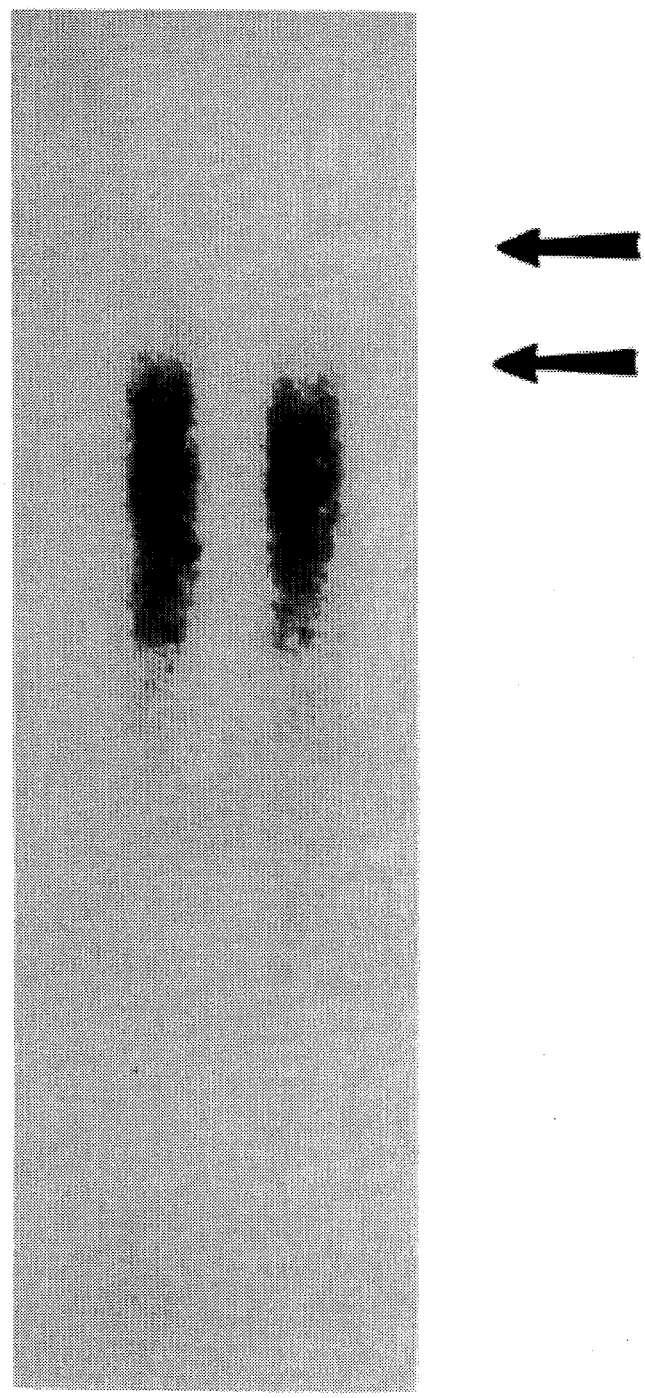
FIG. 3 is an autoradiogram of a 1.4% denaturing agarose gel showing the autoradiographic distribution of aRNA from the first round of aRNA amplification (lane 1) and second round aRNA amplification (lane 2). The arrows indicate the position of 28s (upper arrow) and 18s (lower arrow) ribosomal RNAs.
Figure 4A:
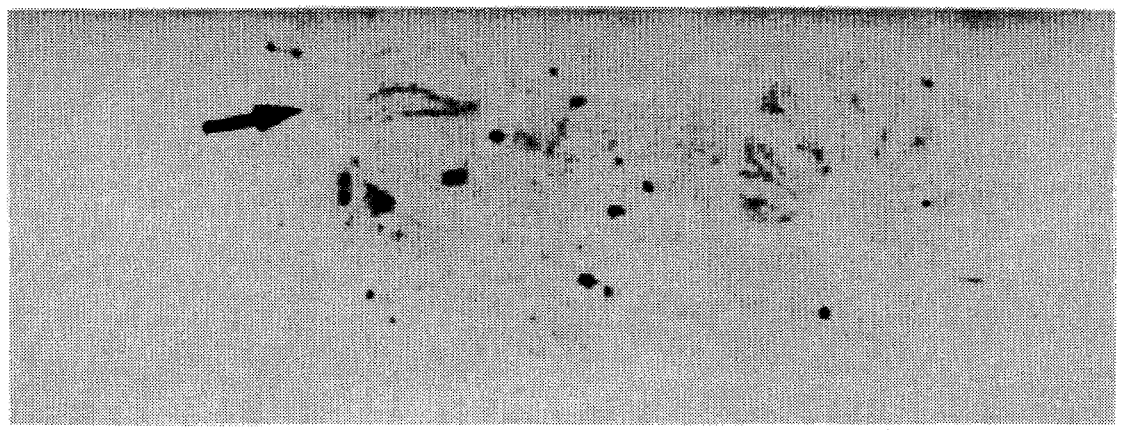
FIG. 4 shows the results of in situ hybridization analysis of selected clones present within the single cell aRNA population.
Figure 4B:
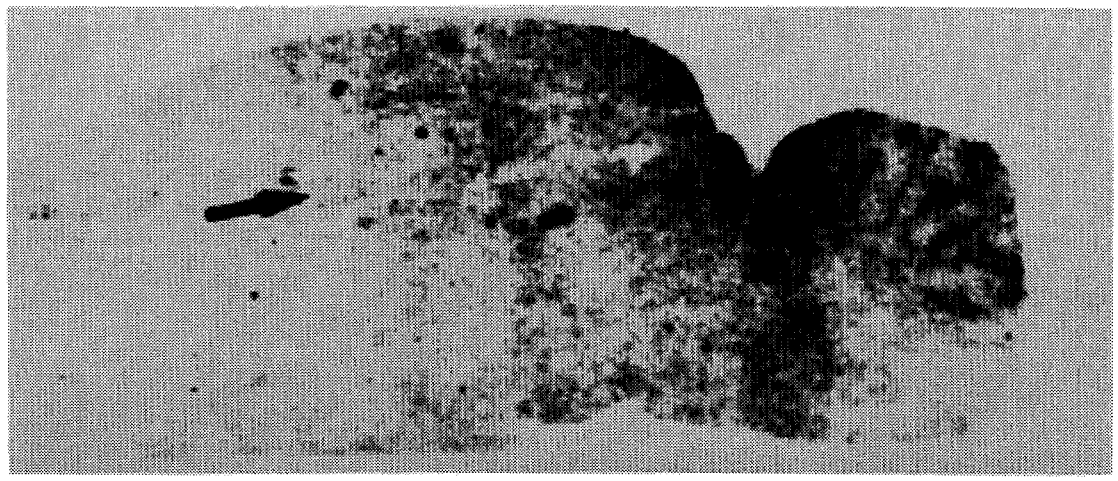
Figure 5A:
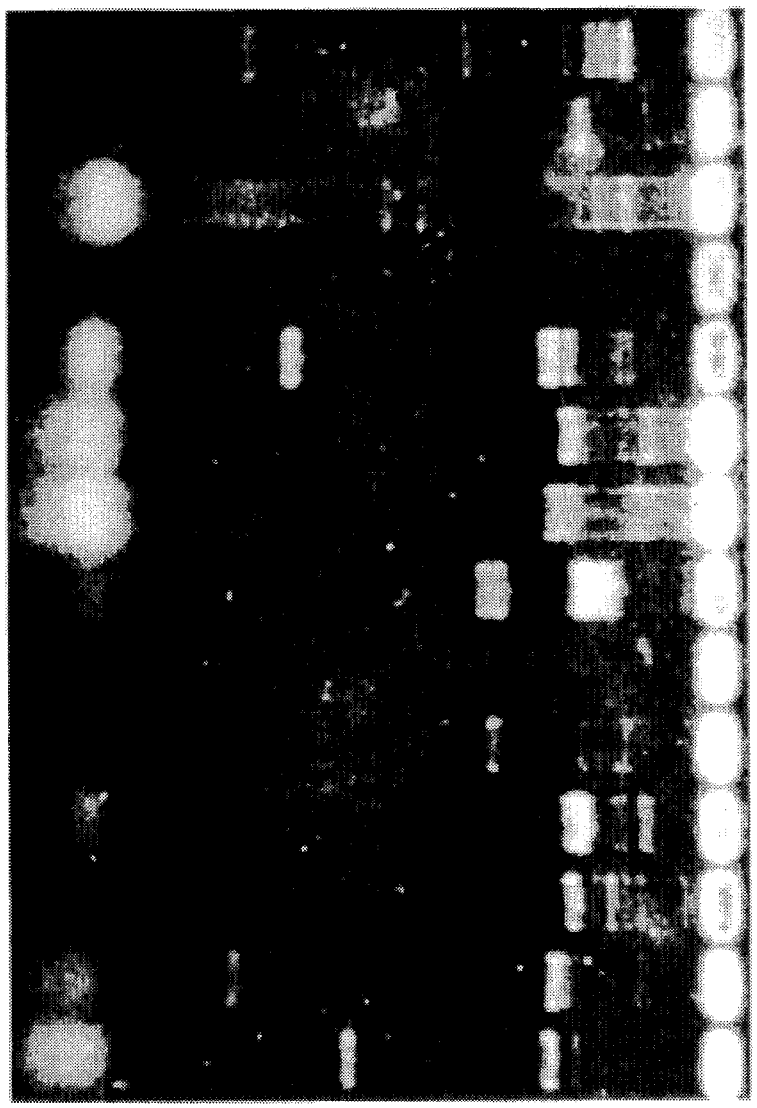
In FIG. 5A, an ethidium bromide stained gel is presented showing that nearly equivalent amounts of the following plasmids were separated on the gel: molecular weight marker (lane 1), glial fibrillary acidic protein (GFAP, lane 2), neurofilament (lane 3), Na channel (lane 5), K channel (lanes 6 and 7), Ca channel (lane 8), GABA receptor (beta subunit, lane 10), c-fos (lane 11), c-jun (lane 12), stimulatory guanyly nucleotide binding protein (lane 13) and inhibitory guanyly nucleotide binding protein (lane 14).
Figure 5B:
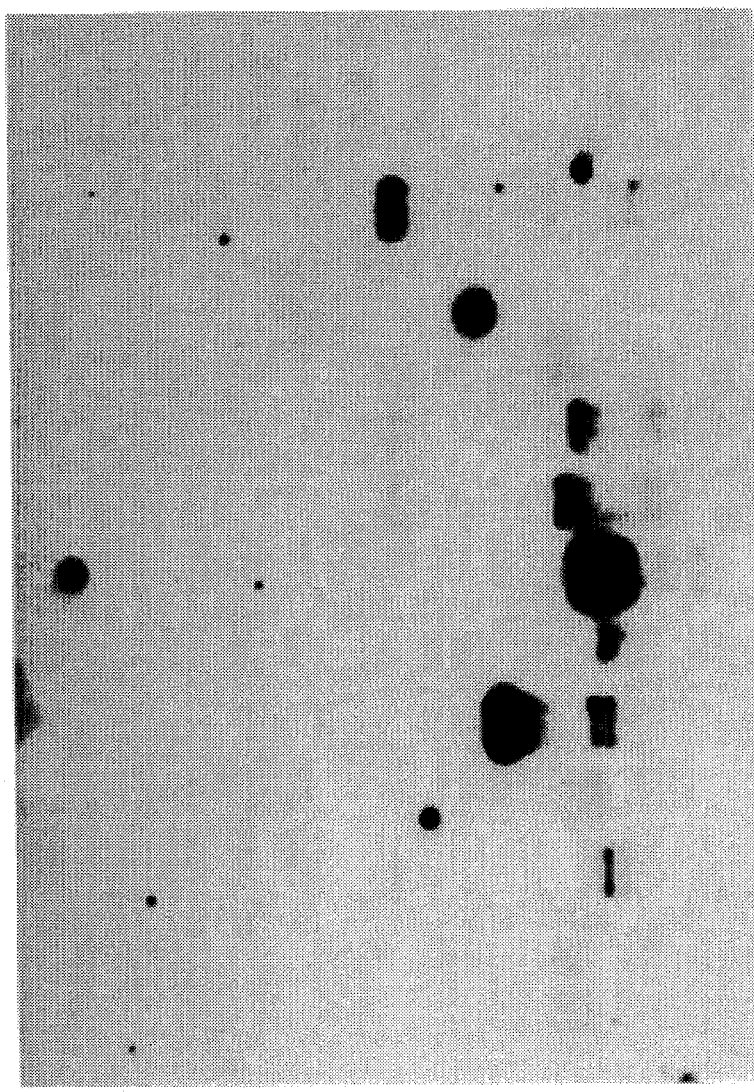
In FIG. 5B, the Southern blot of the gel shown in FIG. 5A is shown after hybridization with radiolabeled aRNA from the equivalent of 1/100th of a single pyramidal cell. The differing intensities reflect differing amount of mRNA for these molecules in the original population of cellular RNA.

An important aspect of the invention concerns the size distribution of the aRNA that is synthesized during the initial amplification procedure, as well as in the second amplification. It has been shown that the size distribution of the first round aRNA is similar to the size of the original cDNA population (VanGelder et al., 1990). In FIG. 3, the size of first and second round radiolabeled aRNA populations are shown. Using this method of amplification, the second round aRNA population will be smaller in size than the first round population, averaging approximately 1 kilobase in size. This population of aRNAs does not represent full length aRNA for many endogenous mRNAs. There are a number of possible reasons for this. It is possible that in situ, the secondary and tertiary structure of the mRNA inhibits the processivity of reverse transcriptase along the mRNA molecule. It is also possible that association of many mRNAs with cellular constituents, such as ribosomes and the cytoskeleton, may make it difficult for reverse transcriptase to make cDNA.

The aRNAs that are generated in this method are extended from regions containing poly-adenosine, which means that most of the aRNAs are made from the 3'-end of the cellular mRNAs. To generate aRNAs that span the entire mRNA sequence would require the use of random sequence oligonucleotides extended at their 5'-ends with the promoter sequence to prime cDNA synthesis. This would work best on isolated poly-A+ mRNAs. In the cell, the ribosomal RNAs would be primed by the random primer method of priming and subsequent amplification.

Regardless of potential limits to the size of aRNA from single cells, it is the more important consideration of aRNA complexity relative to initial mRNA complexity that is of concern in evaluating the usefulness of aRNA in assessing gene expression in single cells, i.e., the abundance of a given mRNA in the original mRNA population of a cell and whether this relative abundance is mirrored in its aRNA population.

The complexity of the aRNA population has been assessed using two approaches: expression profiling and cDNA library screening.

In expression profiling studies of single pyramidal cells, the aRNA obtained from a second round of aRNA amplification was radiolabeled during synthesis and used as a probe to screen Southern blots containing known quantities of the cloned cDNAs for the Ca++, K+, and Na+ channels; the immediate early genes c-fos and c-jun; the beta-subunit of the $GABA_A$ receptor; the alpha-subunits of the guanylynucleotide binding proteins, Gi and Gs; and the neural and glial cell markers glial fibrillary acidic protein (GFAP) and neurofilament, respectively. These cDNAs were chosen for analysis based upon the expectation that the mRNAs encoding these proteins would be present at differing abundances in hippocampal pyramidal cells. Other cDNAs could have been analyzed in the same manner. The relative intensities of hybridization within a blot have been assessed by scanning optical densitometry. The assessment of autoradiographic intensities of known mRNAs and comparison of this intensity to the intensity observed from other mRNAs is "expression profiling". This method assumes that the cDNA synthesis will be constant across the population of mRNAs such that the abundance of any given type of cDNA is proportionate to the total cDNA population as the original mRNA was to the mRNA population, and that the aRNA amplification is linear and does not result in preferential amplification of certain RNA species over others.

It has been found that the cDNA population does, in fact, mirror the mRNA population. It has been demonstrated herein that there does not appear to be a significant difference in the amount of amplification of individual cDNAs into aRNA. Since the cDNA population reflects the mRNA population, the aRNA should, likewise, reflect the abundance of the original mRNA population. While the possibility of preferential amplification of specific sequences cannot be completely excluded, such differences in the amplification would be linear, not exponential as with PCR. Hence, the differences should be small. The expression profile of several different mRNAs within the aRNA population allows interexperimental comparisons since the differences in efficiency of cDNA synthesis and aRNA amplification will serve to normalize the analysis within an experiment.

The expression profile of several individual cells from the rat hippocampus has been analyzed. Using the equivalent of 1/100th of the original starting material of RNA obtained from a hippocampal pyramidal neuron, it has been shown the following rank order of mRNA abundance Ca++ channel>$K^+$ channel>c-jun>>Gs>$Na^+$ channel with undetectable levels of c-fos, Gi and GFAP. Indeed, the major difference between several morphologically similar neurons in which this analysis has been performed is a 50-fold variation in the ratio of Ca Channel to K Channel mRNA. This difference suggests that these two classes of neurons may be functionally distinct and may thus respond to ion signals differently. Alternatively, they may reflect different states of maturity of the neurons. Overall, such data will allow generation of a composite of the relative levels of expression of these and other important regulatory molecules within cells as a function of a wide variety experimental manipulations, developmental events or disease states.

This level of molecular analysis is dictated because cells are functionally classified on the basis expression of specific marker proteins such as the expression of neurofilament protein. The expression of specific proteins or mRNAs within hippocampal cells has been performed and specific classes of cells have been identified, e.g., NMDA-ergic cells. The results from the expression profiling of 15 pyramidal cells allows us to sub-classify these cells on a functional basis derived from the ratio of expression of specific mRNAs within the cells. Two of these cells differed from the others in the ratio of expression of K to Ca channel mRNAs, suggesting that 7.5% of pyramidal cells are of this class. This is not a quantitative measure of the amount of an individual mRNA, on a molar basis, but rather a "self-controlled" comparison of hybridization intensities of these channels in the same aRNA population. Any potential differences in amplification efficiency are normalized by the similar autoradiographic intensities of other molecules used in the expression profiling such as c-jun.

To further assess the complexity of the aRNA generated from a single neuron, radiolabeled aRNAs were used as a probe to identify cDNA clones from a cDNA library so that the complexity of the aRNA population could be determined. This was tested by randomly picking positively hybridizing cDNA clones of differing autoradiographic intensity from the library. After plaque purification, the cDNAs were either plasmid-rescued or PCR amplified and cloned into the bluescript vector. Upon screening of 40,000 cDNA clones from a NG 108 cDNA library, 123 positively hybridizing plaques of varying autoradiographic intensity were isolated. Twelve of these clones were randomly selected to be sequenced and for those DNA sequences that were novel, abundance was determined by Northern blotting and in situ hybridization. This analysis revealed that 8 of the clones were derived from ribosomal RNAs, and 4 of the clones were encoded by mRNAs. The presence of ribosomal aRNAs in the aRNA population is not surprising, given that in making cDNA from total RNA, there is always some ribosomal RNA converted into cDNA. Of the remaining cDNAs, one of them encoded ATP citrate lyase and the other three (11-2c, 11-2b, 24-2c) were novel as determined by nucleic acid and protein database searches. ATP citrate lyase which is present in every cell has been shown to be moderately abundant in total brain RNA. Interestingly, 11-2c, in database searches had sequence similarity with a number of different sequences including the NGF receptor.

The novel cDNAs were random primed and used to screen Northern blots containing total NG 108 and rat hippocampal RNAs. 11-2c and 24-2c hybridization was not detectable after a week-long exposure, while 11-2b hybridized to a band at approximately 2.1 kilobases. The lack of hybridization of 11-2c and 24-2c to Northern blots indicates that the mRNA for these molecules is present in NG 108 cells and hippocampal tissue at less than 0.005% abundance. To determine cellular specificity and relative abundance in the rat brain, 30 base long oligonucleotides were synthesized and labeled with $^{35}$S-dCTP at the 3'-end using terminal deoxynucleotidyltransferase. The film autoradiograms of coronal and sagittal sections of the rat brain through the hippocampus show that the highest level of expression of these mRNAs is in the hippocampus. 24-2c additionally hybridized to the striatal region while 11-2c show no apparent hybridization to other brain regions in this plane. Cellular localization studies show that 11-2c hybridizes to cells in the hippocampus. While it is difficult to say that a given mRNA is absolutely specific (rather than enriched) in a certain cell type, 11-2c is a candidate for being pyramidal cell specific in its expression. If this is true, then the gene for this mRNA may provide a cell specific promoter region which would permit selected expression of downstream sequences in pyramidal cells of transgenic animals. Isolation of pyramidal cell specific mRNAs, followed by promoter characterization may permit a genetic approach to understanding of pyramidal cell function.

Complexity measurement of an RNA population has traditionally been performed by hybridization kinetics. In these studies a vast excess of driver RNA is used to hybridize to all available cDNAs. The degree of hybridization is assessed by determining the amount of RNA present in double-stranded vs. single-stranded fractions as a function of time. The longer the time required for hybridization to be "complete", the more distinct mRNA species there are, and the more complex is the RNA population. This measurement of complexity has an inherent level of sensitivity which is dictated by the specific activity of the probe and abundance of specific RNAs in the probe and driver. Since abundance is an inherent component of a complexity measurement then, when RNA is isolated from a tissue, the abundance of any given RNA is reflective of RNAs within an individual cell as well as those that are present in multiple cells. Thus, complexity measurements on RNA isolated from tissues are not solely measurements of RNA distinctiveness but also a measurement of abundance (those RNAs that can be detected). This suggests that those RNAs that are present in high abundance will be more easily detected than will low abundance mRNAs and that many of those mRNAs that are common to many cells (possibly serving a common function) are represented in higher abundance in a RNA population than mRNAs whose expression is limited to a single cell type. Of the 12 clones that were sequenced, 25 percent of them are low abundance as determined by Northern blot analysis. Since it is probably easier to make cDNA from ribosomal RNAs rather than mRNAs in the single cell because of the size and availability for interaction with the primer, if the ribosomal clones are discounted in a comparison of abundances of aRNA, then the low abundance mRNAs become 50% (¾) of the population of sequences. These results indicate that it is, indeed, easier to isolate low abundance mRNAs from a single cell than from a tissue homogenate.

The aRNAs that are made from individual cells can be cloned so that single cell libraries from presumed different sub-classes of hippocampal cells will be available for screening with radiolabeled probes. While such a library will not contain full-length cDNA clones, it should be of high complexity. The aRNA that is made from single cells need not be cloned to be of use. The aRNA can be used as a specific probe to screen existing cDNA libraries to isolate clones as previously described. aRNA probes from different neurons can be used differentially to screen libraries to isolate clones whose mRNA changes in abundance as a result of cell identity or manipulation. Since it is difficult to work with the RNA isolated from a single cell, it should be possible to use aRNA amplification to increase the amount of RNA from the cell, followed by PCR to amplify specific sequences. This application of single cell molecular biology in this manner may have utility in determining what subtypes of mRNA transcripts for members of gene families, such as the K-channel family, are present in a single cell.

The aRNA amplification procedure may be coupled with selected electrophysiological techniques to determine the molecular influence of neuronal and glial interactions with individual cells in the live slice preparation. In this manner, in the context of naturally occurring neural networks, it may be possible to span the bridge between cellular functioning and molecular biology within the brain.

The present invention may be used to characterize gene expression of a cell when exposed to various stimuli including but not limited to exposure to pharmacoligically active compounds. Expression profiles may be generated from cells under a variety of conditions and/or upon exposure to a variety of agents.

One aspect of the present invention relates to a novel method of identifying opiate-regulated gene transcripts. A method of regulating opiate receptors in neural tissue by altering the relative abundance of mRNAs in neural tissue which code for such receptors is also provided. Opiate receptors in neural tissue may be regulated by altering an RNA population specific for the opiate receptors from selected single cells by microinjecting primer, nucleotides and enzyme into acutely dissociated cells to produce amplified antisense RNA, reamplifying the amplified antisense RNA (aRNA) produced in step A to produce a greater than $10^6$-fold amplification of the original RNA, and detecting messages in the amplified RNA which can be used to characterize cells at the molecular level.

Neural tissues studied in the methods of the present invention include, and are not limited to, the adult rat striatum and NG108-15 cells. While the examples are directed to rat cell lines, other cell lines can be studied. The methods of the present invention are ultimately useful to characterize human cells. The gene transcripts of immediate early cancer cells genes, (IEGs) c-fos and c-jun, $K_v 1$ and $K_v 2$ potassium ion channels, $Na^{++}$ ion channel, $Ca^+$ ion channel, guanine nucleotide-stimulatory protein, Gs and glial fibrillary acidic protein, GFAP, are non-limiting representatives of gene transcripts affected by opioid treatment. Gene transcripts may be tested for response to opioids including, and not limited to, morphine.

Tolerance and withdrawal are the behavioral responses to chronic opiate use. Identification of the genes whose expression are regulated by the use of opioid drugs is necessary to understand the molecular events underlying tolerance and withdrawal. Regulation of neuronal mRNA levels by opioid use almost certainly results from interactions among many CNS cells and is not simply a property of individual neurons. mRNA molecules which change in abundance in response to opioid use can now be identified. The tissues examined included fixed sections from the striatum of the adult rat (an opiate receptor-rich region with normal synaptic connections maintained among heterogeneous neuronal populations until the time of sacrifice) and NG108-15 cells (a homogeneous cell population in which the cellular environment is easily regulated).

Stimulation of δ- and μ-opiate receptor subtypes has been shown to lead to changes in potassium, $K^+$, and calcium, $Ca^{++}$, conductances in postsynaptic neurons examined in vitro (North, R. A. and Williams, J. T., "On the Potassium Conductances Increased by Opioids in Rat Locus Coeruleus Neurons," *J. Physiol.*, 364:265–280 (1985)) Additionally, neurons in opiate responsive neuronal pathways, including cells which do not contain opiate receptors on their plasma membrane, demonstrate changes in protein and mRNA amounts after synaptic activation by opiates. Examples of genes whose abundance change include the immediate-early genes, IEGs c-for and c-jun (Hayward, M. D., et al., "Induction of the c-fos Proto-Oncogene During Opiate Withdrawal in the Locus Coeruleus and Other Regions of Rat Brain," *Brain Res.*, 525:256–264 (1990)) .

Experiments employing aRNA amplification and expression profiling result in consistent findings when studied in situ or in vitro. This approach leads to the identification of alterations in the relative levels of several mRNAs from small amounts of tissue. The cDNAs chosen for this study were those that were generally available for use; contained the 3'-end of the corresponding mRNA, which is important because the synthesized aRNA will always contain more of the 3-prime region of the mRNA; and did not contain poly-A+ tail regions to which the polyuridine region of the aRNA would hybridize.

Results show that expression profiles represent specific hybridization of individual RNAs in the aRNA population to their corresponding cDNA clones. This is clear because no hybridization signals were observed for blots containing vector plasmid DNA without cDNA inserts or prokaryotic DNA used as a molecular size marker. Also, although the cDNAs were present in equivalent amounts on the blots, differences in hybridization intensity were readily apparent. Stringency conditions for both the hybridization and the washing of the blots were sufficient to prohibit nonspecific aRNA-cDNA formation.

The observed changes in mRNA abundances in expression profiles are likely a consequence of altered transcription rates. However, these experiments do not eliminate the possibility that mRNA degradation is also affected. Regardless of the mechanism, changes in the amounts of several mRNAs will result in altered protein synthesis and, consequently, changes in cellular function. An understanding of which mRNA molecules and their corresponding proteins have their relative levels altered by opiate drug use will lead to an understanding of the molecular mechanisms of drug addiction. Studies of the functions of the proteins, in particular with respect to altered ratios of functional proteins encoded by these regulated mRNAs, are needed to determine how they are involved in the behaviors of drug addiction. Additionally, the expression profiles of cells can be studied as indicative of cellular responses to agents useful to treat drug dependence, assist in drug withdrawal or prevent drug activity. The methods of the present invention offer a means for testing agents whose activity can inhibit drug activity.

The invention is further illustrated by means of the following non-limiting examples.

EXAMPLES

Example 1

Patch pipette introduction of cDNA synthesis reagents into single cells

Single cells were obtained from the hippocampus of postnatal Long Evans rats (Charles River Breeding Labs) ranging in ages from postnatal days 5–9. Following decapitation of the animal, the hippocampi were dissected from the rest of the brain, minced into approximately 1 $mm^3$ pieces and incubated at 32°–34° C. for 45 minutes in an Earle's Balanced Salt Solution (EBSS) containing papain (15 U/ml; Worthingtin). All solutions were bubbled continuously with 95% oxygen/5% carbon dioxide. The protease activity was inactivated by using ovomucoid (0.3%) and bovine serum albumin (0.3%). After three washes in the standard bath solution, single cells were obtained by gentle trituration. A small aliquot of this solution was then transferred to a poly-D-lysine-coated 35 mm plastic Petri dish. The cells in suspension were allowed to settle and then were diluted further with additional bath solution (total volume approximately 800 microliters. The freshly dissociated cells were studied within a 3 hour period following dissociation; they were not maintained under long term culture conditions.

Example 2

A 35-mm dish containing freshly isolated hippocampal cells was placed in a chamber attached to the stage of an inverted microscope equipped with Hoffman modulation contrast optics. The cells were examined at 44× and, since the dissociation procedure left neuronal processes relatively intact, many pyramidal cells could be readily identified based on morphological criteria. Only pyramidal cells with a phase-bright soma and distinct apical and basal dendrites were selected for patch recording and intracellular dialysis. The recordings were done at room temperature (22°–24° C.) in a standard bath of physiological saline containing (in mM): 140 NaCl; 2 $CaCl_2$; 1 $MgCl_2$; 10 HEPES; 10 glucose (pH 7.4).

Conventional procedures for pipette preparation, seal formation and recording in the whole-cell configuration were used (Hamill et al., *Pfluger Arch.*, 391:85–100 (1981)). Whole cell macroscopic currents were monitored using a model EPC-7 amplifier (List Electronics, FRG). Patch recording pipettes were fabricated from 1.5 mm outer diameter borosilicate glass (Sutter Instruments Co.) in four stages using a P-80/PC Flaming Brown micropipette puller and fire-polished to a bubble number 4.2–4.4. The pipette solution contained (in mM):120 KCl; 0.5 $CaCl_2$; 1.0 $MgCl_2$; 5.0 EGTA; 10 HEPES; 0.2 dATP,cGTP,dCTP and TTP; 3.0 $Na_3ATP$; 2.0 $Na_2GTP$; 0.01 Na-cGMP (pH 7.2). The typical range of pipette resistance, when filled with this solution was 3–5 megohms.

Example 3

Reamplification Procedure

Figures 1, 1A, 2:
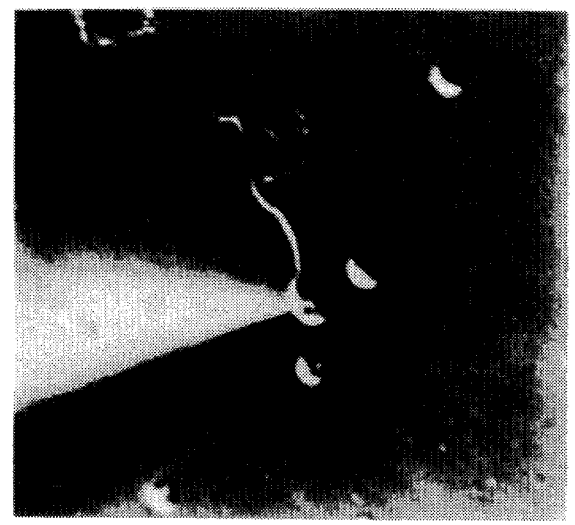
FIG. 2 is a schematic illustrating the reamplification procedure which is used to achieve a million fold amplification of the original RNA population from a single cell.
Figure 2:
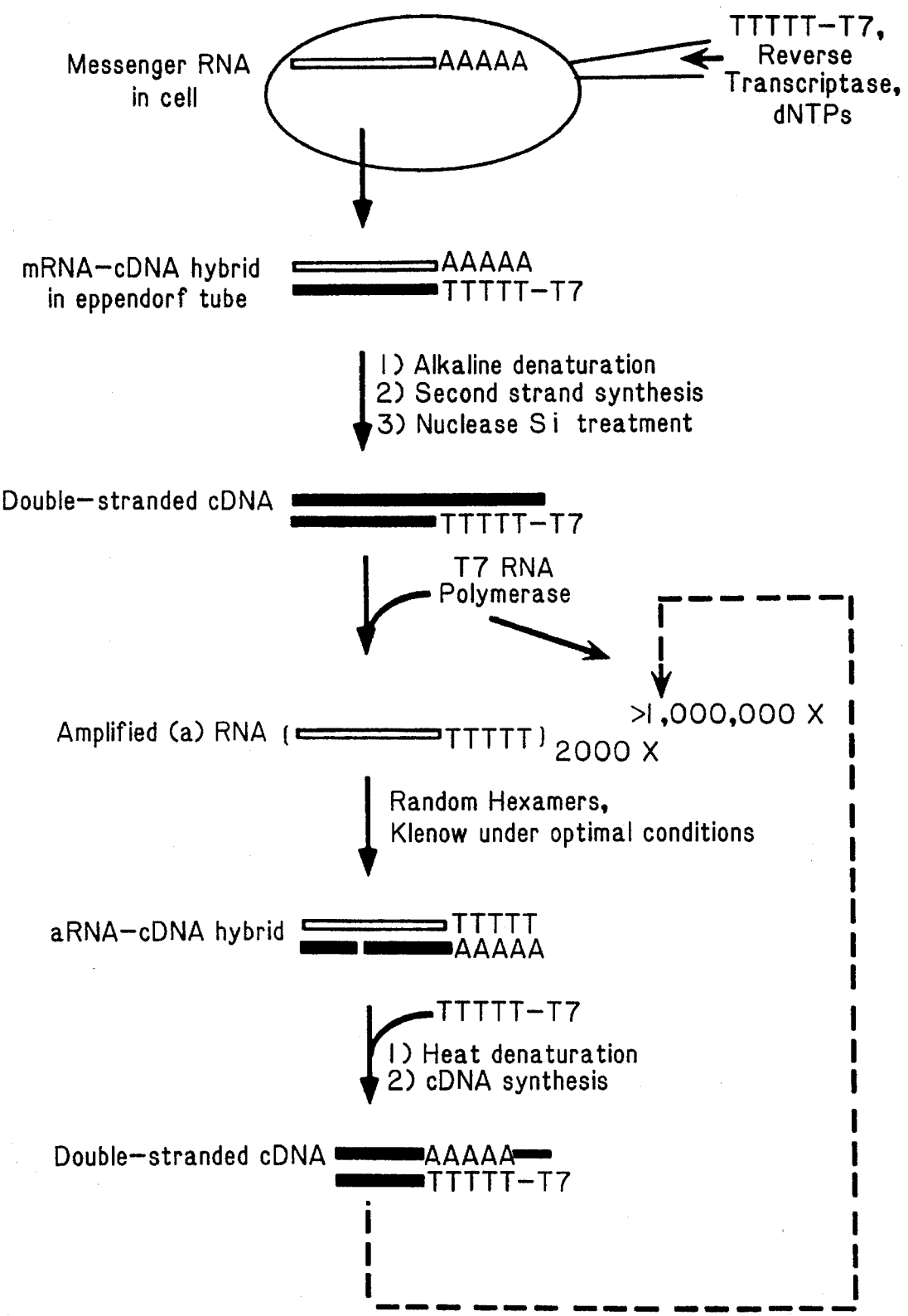

FIG. 2 illustrates the reamplification procedure which was used to achieve a million fold amplification of the original RNA population from a single cell. Single stranded cDNA was generated as described in Example 1. After ethanol precipitation, the DNA is dissolved in 20 microliters of water and heated at 95° C. for 3 minutes. Second strand cDNA synthesis was accomplished by adding 10×2nd strand buffer (5 microliters), dNTPs (250 micromolar), water up to 48 microliters, T4 DNA polymerase (1 microliter) and Klenow (1 microliter) and incubating at 14° C. for a maximum of 5 hours. The sample is then diluted to 450 microliters with water and 50 microliters of 10× S1 buffer, 5 micrograms of *E. coli* tRNA, and 1 unit of S1 nuclease (Boehringer Mannheim) are added and incubated at 37° C. for 5 minutes. After phenol/chloroform extraction and ethanol precipitation, the DNA pellet is dissolved in 22 microliters of water to which are added 2.5 microliters of KFI Buffer and 0.5 microliters of Klenow. This reaction is incubated at 37° C. for 15 minutes, followed by phenol/chloroform extraction and ethanol precipitation. The pellet is dissolved in 20 microliters of TE and drop dialyzed in 10 microliter batches for 4 hours against 50 mls of TE. The DNA recovered from the filter and aRNA is made by mixing the following: DNA sample (2 microliters), 10× Buffer (2 microliters), 100 mM DTT (1 microliter), 250 micromolar ATP, GTP and UTP; 12.5 micromolar CTP and 30 microcuries of CTP (800 Ci/mM, 1 mCi/ml), water (up to 18.5 microliters), RNAsin (–0.5 microliters), and T7 RNA polymerase (1 microliter of 2000 units/microliter; Spicentre Tech.). The mixture is incubated at 37° C. (room temperature can also be used) for 4 hours. After phenol/chloroform extraction and ethanol precipitation, the aRNA (which can be used at this point :for PCR or as a probe) is reamplified by dissolving the pellet in 20 microliters of water and adding 10–100 nanograms of random hexanucleotide primers (this will vary depending on yield of aRNA), 3 microliters of 10× RT Buffer, 3 microliters of 100 mM DTT, dNTPs to 250 micromolar, water to 27.5 microliters, 0.5 microliters of RNAsin, 2 microliters of Reverse Transcriptase and incubating at 37° C. for 1 hour. This mixture is phenol/chloroform extracted and ethanol precipitated. The pellet is dissolved in 10 microliters of water and heat denatured at 95° C. for 2 minutes and quick cooled on ice. Second strand cDNA is synthesized by adding 100 nanograms of oligo-dT-T7 amplification oligonucleotide, 2 microliters of 10× KFI Buffer, dNTPs to 250 micromolar, water up to 17 microliters, 2 microliters of T4 DNA polymerase, 1 microliter of Klenow and incubation at 14° C. for 2 hours. After phenol/chloroform extraction and ethanol precipitation, the pellet is dissolved in 20 microliters of TE, drop dialyzed and an RNA made.

Example 4

Northern blot and in situ hybridization analysis of selected clones present within the single cell aRNA population For Northern blot analysis, novel clones 11-2C, 11-2B, and 24-2C were radiolabeled and used to screen nitrocellulose filters containing RNA from hippocampal tissues (H) and NG108 (NG) cells. 22.5 micrograms of total hippocampal and NG108 RNA were run on a 1.4% denaturing formamide gel, diffusion transferred to nitrocellulose, air-dried and baked in a vacuum oven for 2 hours at 80° C. The blot was then prehybridized for 24–48 hours in a solution containing 50% formamide, 5× SSC, 5× Denhardt's reagent, 1% SDS and 200 mg/ml fractionated salmon sperm DNA. EcoR1-BamH1 fragments from these clones were random-primed using Klenow and a-P32-dCTP to generate probes of high specific activity (108 counts/mg). Each pair of hippocampal and NG108 lanes was probed in the same prehybridization solution with the addition of radiolabeled probe and 1% dextran sulfate for 36–48 hours. The filters were washed under conditions of moderate stringency (3×15 minutes of 2× SSC, 1% SDS at 37 C; 3×15 minutes of 0.1× SSC, 1% SDS at 55 C), air dried and exposed to Kodak XAR-2 film with an intensifying screen at –80° C. for 5 days. Efficiency of RNA transfer was assessed by "reprobing" the portions of the blot previously exposed to 11-2C and 24-2C for cyclophilin, using random-primed probes generated in a similar manner from cDNA for cyclophilin.

Example 5

The invention was used to characterize striatonigral neurons. The antisense RNA populations constructed with this technique avoid several of the shortcomings of cDNA populations built with the polymerase chain reaction including preferential amplification of short cDNAs, propagation of transcription errors and exponential skewing of aRNA abundance.

The role of the dopaminergic nigrostriatal system in controlling the excitability of neostriatal neurons has been intensely studied since it became clear that the loss of this innervation was responsible for the psycho-motor symptoms of Parkinson's disease. Molecular cloning and hybridization studies have revealed that the post-synaptic actions of dopamine are mediated by a family of five G-protein-coupled receptors ($D_1$–$D_2$). Recently, in situ hybridization experiments have suggested that two members of this family— the $D_1$ and $D_2$ receptors—are segregated in the two major efferent populations of the neostriatum that project to the substantia nigra and pallidum.

We have studied acutely-isolated striatonigral neurons identified by retrograde labeling. In these isolated cells, two approaches were used to determine the extent of receptor co-localization. First, using whole-cell and cell-attached voltage-clamp, the modulatory effects of selective $D_1$ and $D_2$ dopaminergic agonist on Na currents were studied. These studies establish that striatonigral neurons not only express $D_1$ receptors, but two functionally significant $D_2$-like receptors as well. Second, to provide an independent assessment and molecular characterization, the RNA from individual striatonigral neurons was amplified and used to probe Southern blots of dopamine receptor cDNAs. Corroborating the patch clamp studies, these experiments show that, contrary to a strict receptor segregation hypothesis, many striatonigral neurons express $D_1$, $D_2$ and $D_3$ receptor mRNAs.

Whole-cell and cell-attached voltage-clamp recordings were made form acutely-dissociated striatonigral neurons that were retrogradely-labeled with rhodamine-impregnated microbeads. Bead injections into the substantia nigra typically labeled about half the cells in frontal sections of the striatum, as well as about half of the cells acutely-dissociated from this region. The ionic currents seen under our recording conditions exhibited biophysical and pharmacological properties similar to those of Na currents described in other brain neurons. These currents play an important role in sub-threshold integration and spike generation in the neostriatum. As described for monoamines in other tissues, the application of dopamine and other dopaminergic agonists produced a reversible decrease in the amplitude of Na currents evoked by depolarizing voltage steps from relatively positive holding potentials. A large percentage (81%, 25/31) of the striatonigral neurons tested responded to the specific $D_1$ agonist SKF 38393. In most of these cells (80%, 20/25), SKF 38393 (1–5 µM) reduced the amplitude of the evoked Na current. The modulation by SKF 38393 appeared to be mediated by $D_1$ receptors as it was blocked by the specific $D_1$ antagonist SCH 23390 (1 µM); n=4). Bath application of 8-bromo-cAMP (1 mM) partially mimicked this effect (n=2), suggesting that the modulation was mediated by $D_1$ receptors that were positively coupled to adenylate cyclase. Furthermore, these receptors appeared to be linked in the signalling pathway by G-proteins as the replacement of GTP in the electrode with the non-hydrolyzable analog, GTP-γ-S, prevented reversal of the modulation by washing (n=4).

In fifty-five percent (23/42) of the neurons tested in whole-cell recordings, the application of $D_2$ agonists quinpirole (n=31) or bromocriptine (n=11) produced a timelocked decrease in evoked current amplitude. The decrease was not a consequence of the enhancement of an outward current as the application of the specific Na channel blocker tetrodotoxin eliminated the evoked current and the change produced by quinpirole (n=5). The response to quinpirole (100 nM) was blocked by the $D_2$ receptor antagonist (−) sulpiride (1 μM, n=5) suggesting that the modulation was mediated by $D_2$-like receptors. As with the modulation produced by $D_1$ agonists, the inclusion of GTP-γ-S in the dialysate prevented reversal of the reduction in current amplitude (n=4), thus implicating G proteins in the signalling pathway.

In about twenty percent (8/42) of our whole-cell recordings, the application of $D_2$ agonists increased the amplitude of the current evoked from −70 mV. (−) Sulpiride antagonized this response, suggesting that it also was mediated by a $D_2$-like receptor (n=4). This enhancement was more common with the application of either bromocriptine (4/10) or quinpirole in the low micromolar range (1–5 μM; 2/4) (rather than in the nanomolar range). Similar responses to $D_2$ agonists were observed in more than half (6/10) of cell-attached patch recordings with bath applied agonists. In this recording configuration, the modulatory responses were dependent upon soluble second messengers. Quinpirole never decreased the evoked current in this paradigm. The $D_1$ agonist SKF 38393, on the other hand, decreased the evoked current in most patches (4/5) as in whole-cell recordings-consistent with the hypothesis that the $D_1$ modulation was cAMP-dependent. These results suggest that the suppression of Na current by $D_2$ agonists was mediated by a membrane delimited pathway, whereas the $D_2$-like enhancement involved a soluble second messenger.

Figure 6A:
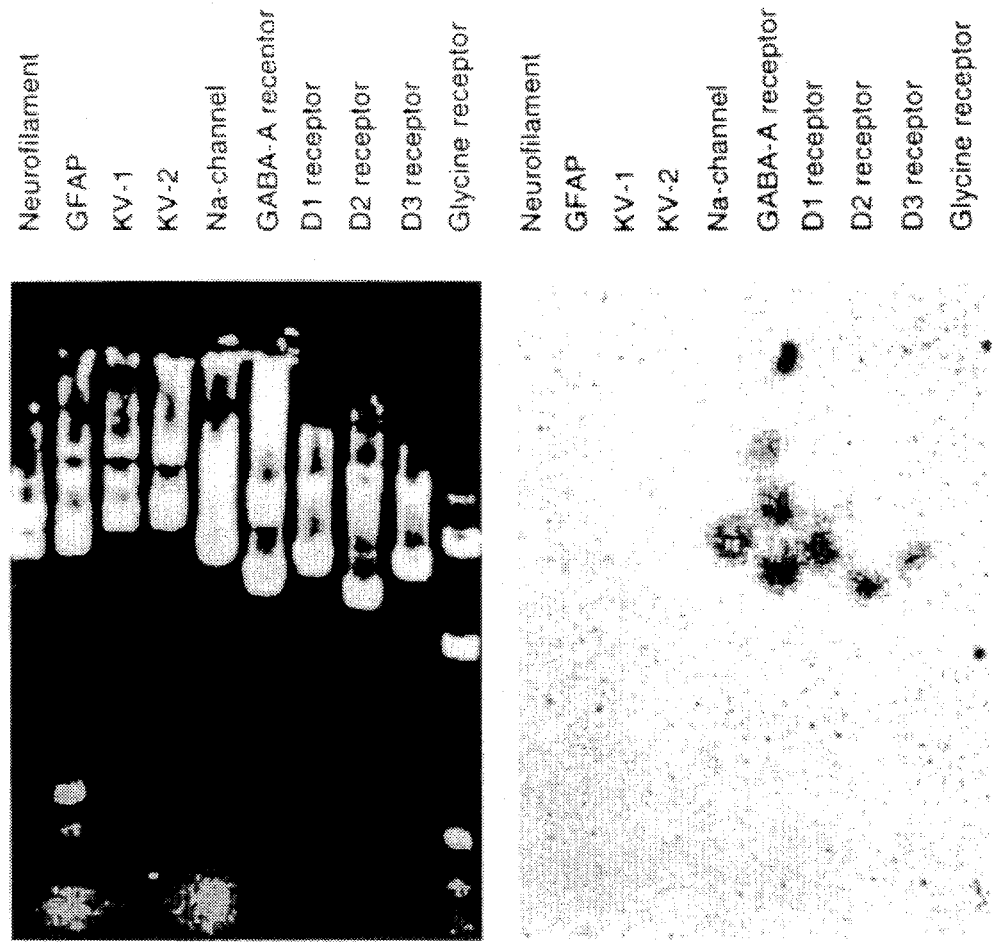
FIG. 6A shows an ethidium bromide stained gel containing cDNAs that were transferred to nitrocellulose for probing with radiolabeled aRNA from a single striatonigral neuron as well as an autoradiogram resulting from an aRNA hybridization to the cDNA clones contained on the Southern blot.

The Dopamine receptor cDNAs were constructed from the mRNA sequences coding for non-homologous regions of the third cytoplasmic domain of the receptors. FIG. 6A shows the ethidium bromide stained gel and the autoradiogram resulting from single-cell aRNA hybridization to the Southern blot. Positive hybridization to cDNAs for $D_1$, $D_2$ and $D_3$ dopamine receptors, the GABA-A receptor and the sodium channel are apparent; longer development times also revealed hybridization to the neurofilament cDNA. All five of the striatonigral neurons subjected to aRNA amplification had detectable levels of $D_1$, $D_2$ and $D_3$ receptor mRNA. These receptor signals did not result from amplification of genomic DNA because aRNA populations did not hybridize to known middle repetitive sequences and hybridization intensity was not uniform. The absence of detectable hybridization to potassium channel (KV-1, KV-2), glycine receptor and glial fibrillary acid protein (GFAP) cDNAs indicates that mRNAs for these proteins were present at very low levels or absent. Other experiments (n=2) have shown that retrogradely-labeled cells possess mRNA for substance P but not enkephalin, in agreement with their identification as striatonigral neurons.

Figure 6B:
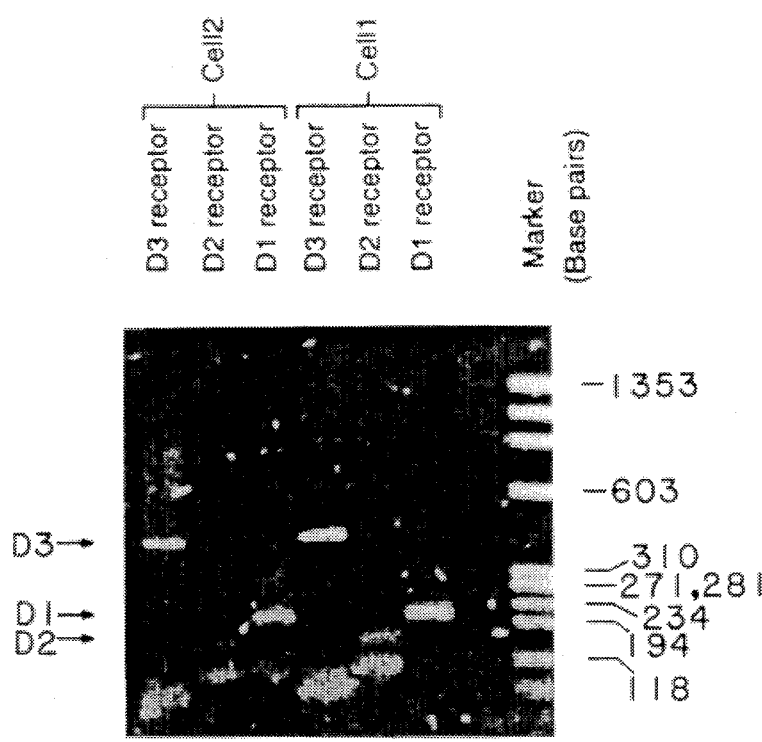
FIG. 6B shows an ethidium bromide stained gel of genetic material from 2 cells.

To further test the specificity of the dopamine receptor hybridization, regions of aRNA molecules coding for the third cytoplasmic domain of each receptor were amplified with the polymerase chain reaction (PCR) and subjected to size analysis. This was accomplished by converting the aRNA into cDNA (using random primers to prime reverse transcription) and then performing PCR using oligonucleotide primers that were specific for regions of the third cytoplasmic loop of the distinct receptor subtypes. For $D_1$ receptor aRNA, this should yield a cDNA of 203 base pairs; $D_2$ and $D_3$ receptor aRNAs should yield cDNAs of 170 and 400 base pairs respectively. In FIG. 6B, the ethidium bromide stained gel of PCR amplified cDNA made from the aRNA of two striatonigral neurons is shown. In cell$_1$, cDNA of the predicted sizes for $D_1$, $D_2$ and $D_3$ receptor mRNA was evident. In cell$_2$, cDNA of the predicted sizes was seen plainly for $D_1$ and $D_3$ receptors, while that for the $D_2$ receptor was faint. As the $D_2$PCR cDNA was from a region of the $D_2$ mRNA transcript that is normally spliced, the absence of a very large, unspliced product in either cell provides further evidence that genomic DNA was not amplification. These experiments establish the specificity of the aRNA hybridization and the supposition that mRNA was amplified, not genomic DNA fragments.

These experiments show that many striatonigral neurons express $D_2$ and $D_3$ receptors, as well as $D_1$ receptors.

Example 6

High frequency stimulation of neuronal synapses results in a potentiation of subsequent evoked responses in the postsynaptic cell. Using the present invention, we have found that a composite of changes in mRNA amounts underlie the cellular response to synaptic potentiation.

Individual CA1 pyramidal cells were identified by their location, morphologic appearance, and response to stimulation of axons in the stratum radiatum. The cells were studied with whole-cell recordings. A ten Hz stimulus train for five seconds resulted in an approximate 100% potentiation of the amplitude of the excitatory post synaptic currents (e.p.s.cs) which lasted more than five minutes after stimulation. This postsynaptic potentiation was prevented by the prior addition of 100 mM D-2-amino-5-phosphonovalerate (APV). APV is a selective noncompetitive N-methyl-D-aspartate (NMDA) glutamate receptor antagonist.

After electrical recording, the cellular contents were aspirated into the patch pipette. Removal of the cell contents was verified by visual inspection. Amplification of the entire poly-A+ RNA population of individual neurons was accomplished by first converting the RNA into cDNA, each molecule of which contains the T7 bacteriophage RNA polymerase promoter. The reagents necessary for cDNA synthesis, including an oligothymidine primer with the T7 RNA polymerase promoter positioned at its five-prime end, reverse transcriptase, and the deoxynucleotide triphosphates, were contained within the recording microelectrode. This solution permits electrophysiological recording and, when in the whole-cell configuration, the reagents may passively diffuse into the cell. The cellular contents were aspirated into the pipette where first strand cDNA synthesis is continued. Following formation of a double-stranded cDNA molecule, antisense aRNA was amplified in vitro with the addition of T7 RNA polymerase. The aRNA molecules ranged in sizes from hundreds of bases to more than two kilobases in length. Importantly, the aRNA size distribution did not differ among the three experimental groups. A similar size distribution of the aRNA population among the three experimental groups indicates that the amplified material is of comparable length and disparities in hybridization to cDNA clones immobilized on Southern blots do not result from large differences in the length of the aRNA. Amplification in this manner results in the synthesis of aRNA in amounts proportionate to the individual mRNAs. Thus, microelectrodes containing reagents for cDNA synthesis may be used to study electrical and pharmacological properties of neurons which remain in contact with endogenous neurons and glia.

Example 7

Opiate-regulated changes in the relative amounts of several mRNAs from the rat striatum were shown using the present invention. Previous studies concerning the effects of opiates have relied upon quantitation of individual RNAs from a population of total RNA isolated from heterogeneous cell populations of the central nervous system (CNS). Additionally, cellular resolution has been achieved using fixed tissue sections employing in situ hybridization. Unfortunately, in situ hybridization will only identify a few mRNAs in a single tissue section and cannot be quantitated. Limited amounts of neural tissue, coupled with the possibility that opiate-regulated mRNAs exist in low abundance in neurons, complicates the identification of mRNAs critical to the development of tolerance and dependence. However, it is likely that multiple gene products, rather than a single protein, are involved in the development of drug addiction. Relative changes in the expression of these genes may, therefore, affect the abundance of many proteins. Consequently, these proteins may act to alter cellular physiology, resulting in tolerance and dependence.

The present study utilized in vitro amplification of the entire polyadenylated (poly-A+) RNA population from the rat striatum or NG108-15 cells to show coordinate changes in the relative amounts of mRNAs for several genes in response to opioid use. This amplification strategy allows for the identification of multiple mRNAs contained in limited amounts of neural tissue which have their relative abundances altered by opioid treatment. The incorporation of the T7 bacteriophage RNA polymerase promoter sequence into the 5' end of the oligo-thymidine-primed cDNA during reverse transcription results in cDNA templates which may be used for in vitro transcription. The abundance of individual cDNAs in the population of total transcripts is representative of the initial mRNA amounts. The synthesized RNA is amplified in a linear fashion and in amounts proportional to the original levels of poly-A+ RNA (aRNA). Because the aRNA is antisense, it may be directly used as a probe to simultaneously screen multiple cDNA clones encoding known mRNAs, a process described as expression profiling, and is the reverse of Northern analysis.

After successful synthesis of cDNA transcripts in situ, the cDNAs were removed from the striatal region and processed into aRNA. Similar processing of poly-A+ isolated RNA from NG108-15 cells resulted in the synthesis of aRNA. Individual samples of $^{32}$P-labeled aRNA were used to probe Southern blots containing multiple cDNA clones. This procedure is a reverse Northern blot and is called an expression profile. A coronal section of the striatum from a rat made tolerant to morphine showed incorporation of $^{32}$P-labeled α-dCTP in all cellular rich regions. This level of incorporation was higher than that obtained in comparable sections without the addition of an oligonucleotide to initiate cDNA synthesis. The size distribution of the synthesized aRNAs ranged from a few hundred bases to more than 2000 bases in length. It is important to note that none of the aRNA could result from the high level of endogenous background because only the specifically primed material would contain the T7 RNA polymerase promoter site. It is this promoter which is utilized to make aRNA. The size distributions did not differ among the aRNA probes. Hybridization of the aRNA to several rat cDNAs chosen because of their potential involvement in addictive behaviors revealed that the relative signals differ between many of these clones. Differing intensities of the hybridization signals are apparent autoradiograms of samples from rat striatum. These results demonstrate the ability to obtain aRNA probes from discrete anatomical regions of the CNS which can be used to characterize the abundance of individual mRNAs from the overall mRNA populations from a limited amount of tissue.

The chronic use of opiates results in stereotypical behaviors associated with drug addiction. These include tolerance (occurring during opioid receptor stimulation) and physical dependence (evident upon withdrawal of opioid use). The requirement for chronic drug exposure as well as the development of characteristic behaviors suggest that changes in gene expression contribute to the development of drug addiction (Mackler, S. A. and Eberwine, J. H., "The Molecular Biology of Addictive Drugs," *Mol. Neurobiol.*, 5:45–58 (1992)). Inhibition of RNA synthesis has been shown to interfere with the development of tolerance to morphine in rats (Cox, B. M. and Osman, O. H., "Inhibition of the Development of Tolerance to Morphine in Rats by Drugs which Inhibit Ribonucleic Acid or Protein Synthesis," *Br J. Pharm.*, 38:157–170 (1970)). Additionally, it has been shown that when the abundance of several mRNAs is changed in discrete brain regions, opioid stimulation or withdrawal occurs. Individual mRNAs which have been examined include c-fos in the striatum (Chang, S. L., Squinto, S. P., Harlan, R. E., "Morphine Activation of c-fos Expression in Rat Brain," *Biochem. Biophys. Res. Comm.*, 157:698–704 (1988)), tyrosine hydroxylase in the locus coeruleus (Guitart, X., et al., "Identification of MARPP-58, a morphine and cyclic AMP-Regulated Phosphoprotein of 58 kD, as Tyrosine Hydroxylase: Evidence for Regulation of its Expression by Chronic Morphine in the Rat Locus Coeruleus," *J. Neurosci.*, 10:2649–2659 (1990)), vasopressin and other neuropeptides in the hypothalamus (Lightman, S. L. and Young, W. S., "Corticotrophin-Releasing Factor, Vasopressin, and Pro-Opiomelanocortin mRNA Responses to Stress and Opiates in the Rat," *J. Physiol.*, 403:511–523 (1988)) and the striatum (Uhl, G. R., et al., "Morphine Alters Preproenkephalin Gene Expression," *Brain Res.*, 459:391–397 (1988)).

A role for gene transcription in the up-regulation of δ-opiate receptors has been suggested (Law, P. Y., et al., "Loss of Opiate Receptor Activity in Neuroblastoma x Glioma NG108-15 Hybrid Cells After Chronic Opiate treatment," *Mol. Pharm.*, 22:1–4 (1982)). For example, in NG108-15 cells, the mRNA for the α-subunit of the guanine nucleotide-binding stimulatory (Gs) protein is also increased after exposure to morphine (von Zastrow, M., et al., "An Approach to the Molecular Biology of Opiate Tolerance: Identification of Opiate-Regulated Transcripts," *NIDA Research Monograph Series: Molecular Approaches to Drug Abuse Research*. US Department of Health and Human Services, 111:85–95 (1991)).

These previous studies have relied upon quantitation of individual RNAs from a population of total RNA isolated from heterogeneous cell populations of the central nervous system (CNS). Additionally, cellular resolution has been achieved using fixed tissue sections employing in situ hybridization. Unfortunately, in situ hybridization will only identify a few mRNAs in a single tissue section and cannot be quantitated. Limited amounts of neural tissue, coupled with the possibility that opiate-regulated mRNAs exist in low abundance in neurons, complicates the identification of mRNAs critical to the development of tolerance and dependence. However, it is likely that multiple gene products rather than a single protein are involved in the development of drug addiction. Relative changes in the expression of these genes may, therefore, affect the abundance of many proteins. Thus, there is a need for a method to identify opiate-regulated gene transcripts. Such identification could be useful in the development of treatments for addiction.

MATERIALS AND METHODS

All enzymes were purchased from Boeringer Mannheim except for AMV reverse transcriptase (Seikagaku Inc.) and T7 RNA polymerase (Epicentre Technologies Inc.). Radionucleotides were purchased from New England Nuclear and the specific activity was 3000 Ci/mmol. cDNA clones that were used in experiments encode for the following neuronal proteins: $Ca^{++}$ channel; $Na^+$ channel; $K^+$ channels; Gs; c-fos; and c-jun; retinoic acid receptor; and GFAP.

Five adult male Sprague-Dawley rats were made opiate-tolerant by daily subcutaneous implantation of delayed-release pellets of morphine for four days (75 mg on day 1, 150 mg on day 2, 225 mg on day 3, and 300 mg on day 4). An identical number of rats were implanted in the same manner with placebo pellets. On the fifth day the rats were killed and the brains were frozen in liquid nitrogen. Coronal sections (11 μm thick) of the striatum were cryostat cut at −14° C., fixed in 4% paraformaldehyde for five minutes, and frozen at −80° C.

An oligonucleotide primer (consisting of the T7 bacteriophage RNA polymerase promoter sequence positioned 5' to an oligo-thymidine segment of 18 to 24 thymidines) was annealed to the RNA in each section at room temperature for 16 hours. The hybridization mixture consisted of the oligonucleotide at a final concentration of two ng/μl in 6×SSC and 50% formamide. The hybridization procedure was performed with equal numbers of control slides without the addition of an oligonucleotide primer for reverse transcription to determine the background level of endogenous priming. The tissue sections were washed in 5×SSC for 4 to 6 hours and then in 0.5×SSC for one hour to remove any primer which had not hybridized to the poly-A+ RNA. In situ transcription proceeded for 60 minutes at 37° C. in a total volume of 150 μl (120 mM KCl; 5 mM $MgCl_2$; 50 mM Tris HCl (pH 8.3); 250 μM each of dATP, dGTP and 50 μM dCTP; 25 μCi $^{32}$P-α-dCTP; 20 U/μL RNAsin and 0.5 U/μL AMV reverse transcriptase).

The synthesis of cDNA was verified by autoradiography to detect the incorporation of $^{32}$P-dCTP. The first strand cDNA transcripts were removed from the glass slides by alkaline denaturation. Second strand synthesis was initiated by hairpin-loop priming and the enzymatic action of T4 DNA polymerase and E. coli DNA polymerase I for 14 to 16 hours at 14° C. This was followed by removal of the hairpin-loop by treatment with 1 unit of S1 nuclease in a 400 μL volume for five minutes at 37° C. Blunt-ending of the double stranded cDNA was accomplished with T4 DNA polymerase for 30 minutes at 37° C. Each enzymatic step was followed by a phenol/chloroform extraction and ethanol precipitation. The initial precipitation used 5 μg of tRNA as a carrier. After cDNA synthesis was completed the template was ready for aRNA amplification.

Equal numbers of NG108-15 cells were treated with media only (control group); 10 nM $^2$D-alanine-$^5$D-leucine-enkephalin (DADLE; stimulated group); or DADLE treatment followed by addition of 100 μM naloxone (precipitated-withdrawal group). The time periods of treatment were 8, 24 or 48 hours (naloxone was added to the withdrawal groups 8 hours prior to the end of the treatment period). The three treatments did not significantly alter the number of cells. The cells were harvested and total RNA isolated with the GTC-LiCl method (Cathala, G., et al., "A Method for Isolation of Intact Translationally Active Ribonucleic Acid," DNA, 2:329–335 (1983)). Poly-A+ RNA was isolated by two passages through oligo-dT cellulose column chromatography (Collaborative Research, Type III). The oligo-dT-T7 primer (identical to the primer used in the IST reactions) was annealed to the poly-A+ RNA via three cycles of 80° C./ice (5 minutes each) and cDNA prepared as previously described for aRNA amplification.

The cDNA templates were suspended in a 10 μl volume and were freed of unincorporated dNTPs by drop dialysis against 50 mL of $ddH_2O$, dNTPs, if present, interfere with RNA synthesis. Equal volumes of cDNA templates, approximately 10% of the total amount, were mixed with transcription solution containing 50 mM Tris-HCl (pH 7.4), 500 μM each of ATP, GTP and UTP; 25 μCi of $^{32}$P-CTP; 5 mM DTT; 10 units of RNase inhibitor; and 1000 units of T7 RNA polymerase. Transcription proceeded for 3 to 4 hours at 37° C. aRNA synthesis was measured by quantitating the incorporation of TCA-insoluble radioactivity. The aRNA was phenol-chloroform extracted and recovered with ethanol precipitation. The size distribution of the aRNA was determined by electrophoreses of approximately 20,000 cpm of incorporated radioactivity of each reaction in a 1.1% agarose-2.5M formaldehyde denaturing gel followed by drying and film autoradiography of the gel.

Several cDNA clones encoding known mRNAs were linearized by restriction digestion and equimolar amounts separated by electrophoresis in 1.0% agarose gels. Amounts of the cDNAs used in each gel ranged from 100 to 800 ng. After depurination in 0.12N HCl for 15 minutes, alkaline denaturation in 0.2N NaOH for 45 minutes and neutralization with Tris HCl pH 7.0 for 45 minutes, the cDNAs were transferred by capillary action to nitrocellulose filter paper and baked at 80° C. in a vacuum oven for two hours. The filters were prehybridized for three hours at 40° C. in five ml of the following solution: 5×SSC; 5× Denhardt's solution; 100 μg/ml salmon sperm DNA; 50% formamide and 1% SDS. The aRNA probes were heat denatured (95° C. for 5 minutes), cooled, and added to bags containing the individual cDNA blots. The aRNA probes were incubated with the blots for 48 hours at 40° C. After hybridization, the blots were washed at 40° C. to a final stringency of 0.5×SSC, 1% SDS, air-dried and directly apposed to XAR film for 2 to 7 days. Reprobing of a used blot with random-primed vector cDNA was performed to check for even transfer of the cDNAs.

Statistical Analysis:

Each autoradiogram was analyzed by scanning laser densitometry. The densitometer readings for glial fibrillary acidic protein (GFAP) (for the IST-derived aRNA probes) and a retinoic acid receptor (for the aRNA samples obtained from the NG108-15 cells) were selected as internal references. These cDNAs were chosen as the internal reference values because of their high relative hybridization signals. The quantitated signals were calculated as a percentage of the internal reference value in each autoradiogram. The mean of each group was used in a two-tailed students t-test with a p value of <0.05 chosen as the threshold for statistical significance. The mean percentages represent three to five separate experiments.

Northern Blots:

Equal amounts (5 μg) of NG108-15 poly-A+ RNA from the three treatment groups at 24 hours of treatment were electrophoresed in 1.1% agarose–2.5M formaldehyde gels and transferred to nitrocellulose filter paper. The cDNA clones for the α-subunit of Gs and c-jun were linearized, radiolabeled by random-priming with $^{32}$P-dCTP to a specific activity of $>10^8$ cpm/μg cDNA, heat-denatured, and hybridized to individual blots for 48 hours at 37° C., washed at a high stringency (a final posthybridization wash in 0.1×SSC, 1% SDS at 50° C.) and apposed to XAR film for 2 days.

In situ Transcription, aRNA Amplification and Expression Profiles:

Following successful synthesis of cDNA transcripts in situ, the cDNAs were removed from the striatal region and processed into aRNA. Similar processing of poly-A+ isolated RNA from NG108-15 cells resulted in the synthesis of aRNA. Individual samples of $^{32}$P-labeled aRNA were used to probe Southern blots containing multiple cDNA clones. This procedure is a reverse Northern blot and is called an expression profile. A coronal section of the striatum from a rat made tolerant to morphine showed incorporation of $^{32}$P-labeled α-dCTP in all cellular-rich regions. This level of incorporation was higher than that obtained in comparable sections without the addition of an oligonucleotide to initiate cDNA synthesis. The size distribution of the synthesized aRNAs ranged from a few hundred bases to more than 2000 bases in length. It is important to note that none of the aRNA could result from the high level of endogenous background because only the specifically primed material would contain the T7 RNA polymerase promoter site. It is this promoter which is utilized to make aRNA. The size distributions did not differ among the aRNA probes. Hybridization of the aRNA to several rat cDNAs chosen because of their potential involvement in addictive behaviors revealed that the relative signals differ between many of these clones. Differing intensities of the hybridization signals are apparent in autoradiograms of samples from rat striatum. These results demonstrate the ability to obtain aRNA probes from discrete anatomical regions of the CNS which can be used to characterize the abundance of individual mRNAs from the overall mRNA populations from a limited amount of tissue.

Reverse Northern Analysis of Striatal aRNA in Morphine-Treated Rats:

Comparison of the expression profiles after five days of morphine administration with placebo-treated rats revealed a significant decrease in the hybridization signal for the voltage-sensitive $K_v2$ ion channel (from 83%±24 to 2%±2, p<0.05). There was also a reduction in hybridization of aRNA to the $K_v1$ ion channel (from 156%±57 to 50%±25), without clear changes in other ion channels studied. During the same time period of drug exposure, a trend toward an increase in c-fos levels (55%±43 as compared to 156%±7) without alterations in c-jun or selected members of the guanine binding (G) protein receptor group occurred.

Analysis of NG108-15 Cells After DADLE Treatment:

Experiments were next performed in vitro to study a homogeneous population of opiate-receptor expressing cells, as well as to further describe the time course of changes in mRNA amounts after opiate use, as well as precipitated-withdrawal. Treatment of NG108-15 cells with DADLE for 24 or more hours results in maximal δ-opiate receptor down regulation. Precipitated-withdrawal using naloxone produces maximal receptor up-regulation within eight hours. In the present experiments, equal numbers of cells from control, stimulated, and withdrawn treatment groups were detached from the plates, the poly-A+ RNA isolated, and processed for aRNA amplification.

Stimulation with DADLE resulted in a reduction in the signals for the potassium ion channels $K_v1$ (from 9.13%±2.82 in control cells to 0.36%±0.36 at 48 hours of treatment; p<0.05) and $K_v2$ (from 5.36%±3.46 to 0.08%±0.08 at 48 hours of treatment). The decline was largest after 48 hours of DADLE application. In comparison, the signal for a voltage-sensitive $Ca^{++}$ channel remained unchanged while that for a voltage-sensitive $Na^+$ channel increased slightly and was statistically significant at eight hours (23.55%±7.62 versus 11.04%±2.19, p<0.05). In addition, increases in the hybridization signals were associated with DADLE treatment at all three time periods for the α-subunit of the Gs protein and for the two immediate early genes (IEGs) c-fos and c-jun (for c-jun 58.25%±18.34 (p<0.01) at eight hours, 10.74%±3.66 (p<0.05) at 24 hours, and 55.02±5.63 (p<0.01) compared to control (1.39%±1.28)).

Hybridization signals were observed to change with naloxone treatment alone for eight hours and for precipitated-withdrawal after 16 or 40 hours of DADLE exposure. A similar tendency towards reduction in the signals for the two $K^+$ channels occurs with naloxone treatment alone. Naloxone precipitated-withdrawal was not associated with a dramatic reduction in relative mRNA amounts for the two $K^+$ ion channels. However, this treatment was associated with an increase in the signal for the calcium channel (49.00%±8.86 at 24 hours and 51.39%±10.28 at 48 hours compared to 14.87%± 2.77; p<0.05). Naloxone precipitated-withdrawal also led to an increase in the signal for the sodium channel (significant at 48 hours (35.23%±9.99 versus 11.04%±2.19; p<0.05), the Gs α-subunit (not statistically significant), and c-fos (15.73%±7.32 versus 1.99%±0.98 at 48 hours, p< 0.05) and c-jun (29.41%±13.63 at eight hours (p<0.05), 43.86±13.61 at 24 hours (p<0.01), and 48.61%±19.47 at 48 hours (p<0.05) compared to 1.39%±1.28). Naloxone treatment alone for eight hours had a greater effect upon c-jun mRNA levels (29.41%±13.63) as compared to c-fos (8.68%± 5.08).

In order to test whether the above results correlate with the standard Northern blotting technique, radiolabeled cDNA probes for Gs and c-jun were hybridized to a set of blots containing equal amounts of poly-A+ RNA from NG108-15 cells in the three treatment groups. Both DADLE use and naloxone precipitated-withdrawal for 24 hours increased the absolute amount of Gs mRNA when compared to control (respectively 2.27-fold and 1.28-fold). Both DADLE use (a 4.56 fold-increase) and naloxone precipitated-withdrawal (3.19-fold increase) were associated with increases in mRNA for c-jun after 24 hours of treatment. These results show that the relative changes in the signals obtained from the aRNA-cDNA expression profiles are similar to those observed for absolute amounts of mRNA obtained from Northern blots. This more conventional method of identifying opiate-regulated mRNAs, however, requires multiple screenings and large amounts of tissue to provide enough mRNA to determine the abundance of multiple distinct mRNAs. Furthermore, and most importantly, the relative changes between several mRNAs would not be apparent.

RESULTS

It has been discovered that chronic opioid administration is associated with decreases in the relative levels of mRNAs for two potassium ion channels. This result likely reflects a decrease in the amount of potassium channel proteins $K_v1$ and $K_v2$ and, consequently, a down-regulation of potassium channel function. This observation may represent a molecular change contributing to tolerance. Studies with single opiate responsive neurons in the locus coeruleus as well as individual neurons in the spinal cord have provided electrophysiological evidence for $K^+$ channel activation and membrane hyperpolarization upon acute opioid administration. In light of these previous studies, it is believed that there is a decrease in $K^+$ channel mRNA and potentially $K^+$ conductance in post-synaptic neurons or glia. Alternatively, this difference may be reflective of acute versus chronic opiate treatment, or tissue specific differences in responsiveness, or opiate receptor subtype specific effects. A nonspecific general reduction in ion channel gene expression induced by chronic opioid use is not supported by the present data because morphine administration for five days did not produce relative reductions of striatal mRNA molecules for the voltage-sensitive calcium, sodium, and GABA-A channels. The effects of morphine use on the mRNAs encoding voltage-sensitive ion channels in the rat striatum for the time period examined in this study is specific for potassium channel mRNA.

No significant increases in relative levels of c-fos and c-jun after five days of morphine treatment were observed. In accordance with these findings, expression of immediate early genes (IEGs) c-fos and c-jun usually declines within hours of activation in response to several types of stimuli and would be expected to show similar results for the times examined in this study. Previous experiments performed in cell culture and in the rodent CNS, including after opioid administration and opioid withdrawal, have shown increases in IEG levels. However, this does not preclude the possible selective and prolonged activation of c-fos, c-jun, and other IEGs that could occur in distinct classes of neurons in the CNS but cannot be identified by IST-aRNA of tissue sections containing multiple types of cells.

The apparently unchanged levels of the α-subunit of guanine nucleotide-stimulatory protein, Gs, and the G protein coupled $\beta_1$ and $\beta_2$ adrenergic receptors suggests the absence of heterologous receptor mRNA regulation by morphine within the rat striatum. Gs mRNA has been shown to be regulated by opioid use in NG108-15 cells. Heterologous receptor regulation (stimulation of opiate receptors resulting in changes in the amount and/or function of other membrane receptors) is not apparent in the rat striatum after five days of morphine treatment. However, heterologous receptor regulation may occur in other areas of the rat CNS or, as discussed above for the IEGs, may be limited to small numbers of striatal cells.

Characterization of relative mRNA amounts at a single time point of morphine treatment might miss changes which occur at discrete time periods. However, the aim of this study was to identify chronic alterations in mRNA amounts in the rat striatum in order to examine factors responsible for the maintenance of tolerance, a behavior which remains present for weeks to months. Morphine administration was associated with a specific and significant alteration in the relative amounts of one class of striatal mRNAs that were examined, the voltage-sensitive potassium channel mRNAs $K_v1$ and $K_v2$. This finding shows that opioid use does not lead to nonspecific activation of many genes. Thus, identification of opiate-regulated gene transcripts should be helpful in functional studies of tolerance.

The results of morphine treatment in adult rats are distinct from treatment of NG108-15 cells with $^2$D-alanine-D-leucine-enkephalin (DADLE), a δ-opiate receptor agonist, over a time course of eight to 48 hours. This treatment was associated with changes in the abundance of several mRNAs. Experiments using the homogeneous population of opiate receptor-expressing cells, NG108-15 cells, avoids the under-representation of opiate-regulated mRNAs in tissue samples containing diverse types of neurons and glia (such as in the striatum), in which large amounts of RNA isolated from cells which are not opiate responsive would obscure changes in specific mRNAs regulated by opioids. A relative reduction occurred in potassium voltage-sensitive ion channel $K_v1$ and $K_v2$ mRNA levels, similar to that observed in the rat striatum. This early and pronounced decrease in signals for these potassium channels also seems likely to represent a down-regulation of potassium ion channels in response to continued opiate receptor stimulation. In contrast to these findings, a significant increase in relative levels of mRNA for a brain voltage sensitive sodium ion channel occurred after eight hours of DADLE treatment. The relative increase in sodium channel mRNA appears to remain for the entire 48 hour period of study. This change in an ion channel not known to be directly affected by opiate stimulation suggests that opioid use has had distinct effects in different cell types. NG108-15 cells contain only the δ-subtype of opiate receptors, while the rat striatum contains μ-, δ-, and κ-opiate receptors. It is possible that the different effects on the relative amounts of $Na^+$ channel mRNA observed in this study is due to activation of distinct opiate receptor subtypes or results from the interaction of heterogenous cells within different neuronal and glial environments. The effects that a relative increase in sodium channel mRNA would have upon neuronal excitability are unclear at the present time.

The increase in guanine nucleotide-stimulatory protein, Gs, mRNA in NG108-15 cells after DADLE use is supported by findings from the Northern blot analysis using the cDNA clone for Gs to probe NG108-15 RNA. The significance of this increase in a member of the G protein group whose function is not directly altered by opiate use may be due to a compensatory up-regulatory mechanism. This data suggests that increased activity of Gi, the G-protein coupled to the δ-opiate receptor, may lead to an increase in Gs mRNA and protein levels to counter the increase in Gi activity. The observed increase in relative amounts of mRNAs for the IEGs c-fos and c-jun may represent an initial trigger in the development of the molecular response to addictive drug use. The relative increase in c-jun mRNA levels also is supported by the Northern analysis of NG108-15 RNA. IEGs work by increasing the transcription of specific genes and are independent of protein synthesis.

Precipitated-withdrawal by naloxone, an opiate antagonist, also produces changes in the relative amounts of several neuronal mRNA molecules. A trend towards a decrease in potassium ion channel mRNAs again appears, but does not result in as large a reduction in mRNA as seen with DADLE use alone. Naloxone may modulate endogenous activation of $K^+$ channel mRNA in NG108-15 cells. However, opioid pretreatment limits this naloxone effect. Also, an increase in the signal for the calcium channels occurs with precipitated-withdrawal. The effects of increases in calcium and sodium channels on neuronal activity suggests a mechanism to explain the neural hyperexcitability which is characteristic of withdrawal in animal and clinical studies. This may occur by lowering the threshold for initiation of action potentials in excitable cells which contain more voltage-sensitive sodium or calcium channels. Increases in c-fos and c-jun occur with both naloxone use and precipitated-withdrawal. These increases persist for 48 hours and may play a role similar to that hypothesized for IEG activation after opiate receptor stimulation. In NG108-15 cells, activation of c-fos and c-jun occurs with both DADLE and naloxone application. Therefore, these IEGs may represent initial molecular triggers in responses leading to a cascade of gene activation resulting in tolerance and physical dependence.

The observed changes in mRNA abundances in expression profiles are likely a consequence of altered transcription rates. However, these experiments do not eliminate the possibility that mRNA degradation is also affected. Regardless of the mechanism, changes in the amounts of several mRNAs will result in altered protein synthesis and, consequently, changes in cellular function. An understanding of which mRNA molecules and their corresponding proteins have their relative levels altered by opiate drug use will lead to an understanding of the molecular mechanisms of drug addiction. Studies of the functions of the proteins, in particular with respect to altered ratios of functional proteins encoded by these regulated mRNAs, are needed to determine how they are involved in the behaviors of drug addiction.

Example 8

A kit is provided which is useful to characterize cells. The kit comprises one or more containers comprising primer, nucleotides and polymerase. In some embodiments, the primer comprises an oligo-dT-T7, an oligo-dT-T3 or an oligo-dT-$SP_6$ amplification oligonucleotide; the polymerase comprises reverse transcriptase; and another primer comprises random hexanucleotides. In one embodiment, the kit comprises a first container comprising a first primer, a second container comprising nucleotides, a third container comprising polymerase and a fourth container comprising a second primer. In one embodiment, the kit comprises a first container comprising an oligo-dT-T7, an oligo-dT-T3 or an oligo-dT-$SP_6$ amplification oligonucleotide, a second container comprising nucleotides, a third container comprising reverse transcriptase and a fourth container comprising random hexanucleotides.

The present invention is not intended to be limited to the examples above.

What is claimed is:

1. A method for characterizing mRNA in a single cell comprising the steps of:

amplifying RNA in a single cell by microinjecting into a single cell an amplification primer, reverse transcriptase and nucleotides to synthesize a first strand cDNA from cellular mRNA; harvesting the cellular contents, including the first strand cDNA; synthesizing double-stranded cDNA from the first strand cDNA; and producing aRNA from the double stranded cDNA by addition of an RNA polymerase capable of recognizing the amplification primer;

reamplifying the produced aRNA by adding random hexanucleotide primers; extending the hexanucleotide primers with a reverse transcriptase to form first strand cDNA; synthesizing double stranded cDNA from the first strand cDNA using the amplification primer; and producing reamplified aRNA from the double stranded cDNA by addition of an RNA polymerase capable of recognizing the amplification primer; and detecting specific RNA molecules in the reamplified aRNA.

2. The method of claim 1 wherein the amplification primer comprises oligo-dt-T7, oligo-dt-T3 or oligo-dT-$SP_6$.

3. The method of claim 1 wherein the cell is a live acutely dissociated brain cell.

4. The method of claim 1 wherein the cell is first treated with an opioid compound prior to having its mRNA characterized.

5. The method of claim 4 further comprising the step of comparing the specific RNA molecules in the reamplified RNA of the opioid treated cell with a nontreated cell.

6. The method of claim 1 wherein the specific mRNA molecules are detected by reverse Northern blotting.

* * * * *